(12) United States Patent
Kondo et al.

(10) Patent No.: US 12,119,116 B2
(45) Date of Patent: Oct. 15, 2024

(54) APPARATUS, INFORMATION PROCESSING METHOD, AND COMPUTER-READABLE RECORDING MEDIUM FOR DISEASE CORRELATION AND INFERENCING

(71) Applicant: DEEPEYEVISION INC., Shimotsuke (JP)

(72) Inventors: Yusuke Kondo, Shimotsuke (JP); Hidenori Takahashi, Shimotsuke (JP)

(73) Assignee: DEEPEYEVISION INC., Shimotsuke (JP)

( * ) Notice: Subject to any disclaimer, the term of this patent is extended or adjusted under 35 U.S.C. 154(b) by 0 days.

(21) Appl. No.: 18/562,901

(22) PCT Filed: Sep. 26, 2022

(86) PCT No.: PCT/JP2022/035567
§ 371 (c)(1),
(2) Date: Nov. 21, 2023

(87) PCT Pub. No.: WO2023/054219
PCT Pub. Date: Apr. 6, 2023

(65) Prior Publication Data
US 2024/0233947 A1    Jul. 11, 2024

(30) Foreign Application Priority Data

Sep. 30, 2021   (JP) .................. 2021-161483

(51) Int. Cl.
*G16H 50/20* (2018.01)
*G06T 7/00* (2017.01)
(Continued)

(52) U.S. Cl.
CPC .......... *G16H 50/20* (2018.01); *G06T 7/0012* (2013.01); *G06V 10/44* (2022.01); *G06V 10/764* (2022.01);
(Continued)

(58) Field of Classification Search
None
See application file for complete search history.

(56) References Cited

U.S. PATENT DOCUMENTS

| 2014/0161327 | A1* | 6/2014 | Motomura ............ G06T 7/0014 382/128 |
| 2017/0103168 | A1* | 4/2017 | Chen ...................... G16H 50/20 |
| 2021/0000343 | A1 | 1/2021 | Kurihara et al. |

FOREIGN PATENT DOCUMENTS

| JP | 2014-113364 A | 6/2014 |
| JP | 2021-39748 A | 3/2021 |
| WO | 2019/142910 A | 7/2019 |

OTHER PUBLICATIONS

Parisot, Sarah, et al. "Disease prediction using graph convolutional networks: application to autism spectrum disorder and Alzheimer's disease." Medical image analysis 48 (2018): 117-130. (Year: 2018).*

(Continued)

*Primary Examiner* — Samah A Beg
(74) *Attorney, Agent, or Firm* — PROCOPIO, CORY, HARGREAVES & SAVITCH LLP

(57) ABSTRACT

An information processing apparatus that comprises a processor configured to: acquire an image acquisition unit that acquires a medical image; extract one or more image feature values from the medical image; infer one or more diseases predicted from the medical image based on the one or more image feature values and a classification basis, the classification basis being a set of C basis vectors with each basis vector representing correlations between a disease of a set of C diseases and other diseases by using a vector of a certain dimension, wherein C is an integer of 2 or more; and output results identifying the one or more inferred diseases.

13 Claims, 9 Drawing Sheets

(51) Int. Cl.
  G06V 10/44    (2022.01)
  G06V 10/764   (2022.01)
  G06V 20/70    (2022.01)
  G16H 30/40    (2018.01)
(52) U.S. Cl.
  CPC ............. *G06V 20/70* (2022.01); *G16H 30/40* (2018.01); *G06T 2207/30096* (2013.01)

(56) References Cited

OTHER PUBLICATIONS

Sun, Zhenchao, et al. "Disease prediction via graph neural networks." IEEE Journal of Biomedical and Health Informatics 25.3 (2020): 818-826. (Year: 2020).*

Zhu, Yonghua, et al. "Interpretable learning based dynamic graph convolutional networks for alzheimer's disease analysis." Information Fusion 77 (2022): 53-61. (Year: 2022).*

Chakravarty, Arunava, et al. "Learning decision ensemble using a graph neural network for comorbidity aware chest radiograph screening." 2020 42nd Annual International Conference of the IEEE Engineering in Medicine & Biology Society (EMBC). IEEE, 2020. (Year: 2020).*

Mao, Chengsheng, Liang Yao, and Yuan Luo. "Imagegcn: Multi-relational image graph convolutional networks for disease identification with chest x-rays." IEEE transactions on medical imaging 41.8 (2022): 1990-2003. (Year: 2022).*

Gao, Jianliang, et al. "Similar disease prediction with heterogeneous disease information networks." IEEE Transactions on NanoBioscience 19.3 (2020): 571-578. (Year: 2020).*

Patent Cooperation Treaty, International Search Report, Application No. PCT/JP2022/035567, dated Nov. 22, 2022, in 4 pages.

Patent Cooperation Treaty, WOSA, Application No. PCT/JP2022/035567, dated Nov. 22, 2022, in 3 pages.

Patent Cooperation Treaty, WOSA, Application No. PCT/JP2022/035567, dated Nov. 22, 2022, in 9 pages.

* cited by examiner

APPARATUS, INFORMATION PROCESSING METHOD, AND COMPUTER-READABLE RECORDING MEDIUM FOR DISEASE CORRELATION AND INFERENCING

CROSS-REFERENCE TO RELATED APPLICATION

The present application is based on Japanese Patent Application No. 2021-161483 filed on Sep. 30, 2021, the contents of which are incorporated herein by reference.

TECHNICAL FIELD

The present disclosure relates to an information processing apparatus, an information processing method, and a computer-readable recording medium.

BACKGROUND ART

In the medical field, machine learning has been increasingly utilized in computer-assisted detection (CADe) and the like, where CADe detects diseases such as diabetic retinopathy by applying machine learning such as deep learning to, for example, photographs (hereinafter referred to as "fundus images") acquired through photographing by a standard non-mydriatic fundus camera.

CITATION LIST

Patent Literature

Patent Literature 1: International Publication No. WO 2019/142910

SUMMARY OF INVENTION

Patent Literature 1 discloses a diagnostic support apparatus that identifies an area with abnormal blood circulation in a fundus image using a learned model that has learned a relationship between fundus images, which are images of the fundus, and areas with abnormal blood circulation in the fundus images based on the fundus images and the areas with abnormal blood circulation identified based on fluorescein fundus angiographic images.

Now, there are more than 100 types of retinal disease including both localized diseases in which lesions are limited to a small area and diffuse diseases in which lesions are spread to a large area. Furthermore, there are cases in which a single lesion is caused by multiple diseases, and under the present circumstances, it is difficult to highly accurately diagnose one or more retinal diseases anticipated from a fundus image by applying CADe that encompasses all retinal diseases to the single fundus image.

By developing CADe dedicated to each retinal disease, it will be possible to diagnose each retinal disease with high accuracy, but the time and effort taken to develop dedicated CADe for each of more than 100 retinal diseases are immeasurable.

It is considered that in actual diagnosis, the doctor makes a final determination using not only information about a fundus image, but also information about correlations among diseases, but the current CADe has not yet been able to take such relations among diseases into consideration.

Thus, an object of the present disclosure is to provide an information processing apparatus, an information processing method, and a computer-readable recording medium that can infer one or more diseases from a medical image acquired by photographing an examination region of a patient.

An information processing apparatus according to one aspect of the present disclosure comprises: an image acquisition unit that acquires a medical image; an image feature extraction unit that extracts one or more image feature values from the medical image; an inference unit that infers one or more diseases predicted from the medical image based on the one or more image feature values and a classification basis, the classification basis being a set of basis vectors that represent correlations between each of the diseases and other diseases by using a vector of a certain dimension; and an output unit that outputs results inferred by the inference unit.

By using the classification basis that has learned correlations among diseases in inferring a disease, the present aspect allows one or more diseases to be inferred among a wide variety of diseases. By using the classification basis, the present aspect can utilize information about correlations among diseases not utilized conventionally, and consequently can make inferences with higher accuracy than when inferences are made only from medical images.

In the information processing apparatus, the image feature extraction unit may acquire the one or more image feature values by inputting the medical image to a first learned model; and the first learned model may be a learned model that have learned to estimate one or more image feature values from a medical image. The present aspect makes it possible to easily acquire one or more image feature values having a desired accuracy.

In the information processing apparatus, the classification basis may be obtained by causing a second machine learning model to do learning, where the second machine learning model accepts data embedded with label information about a plurality of medical images labeled with one or more diseases as input data, and outputs a feature that has learned correlations among diseases. The present aspect makes it possible to easily acquire a classification basis having a desired accuracy.

In the information processing apparatus, the data accepted as the input data may be graph data embedded with the label information about the plurality of medical images labeled with one or more diseases, the label information being in multi-hot vector form; and the second machine learning model may be a graph convolutional neural network, with global max pooling (GMP) being applied in a final convolutional layer. The present aspect enables effective downsampling, leaving important image feature values.

In the information processing apparatus, the graph data may include a node corresponding to a disease or a lesion; and the inference unit may infer one or more lesions in addition to one or more diseases from the medical images. The present aspect makes it possible to infer not only diseases, but also lesions related to the diseases from medical images, and present the lesions as inference results. Consequently, a user who utilizes the inferred results can work out a treatment strategy by taking into account, for example, information about lesions and the like common to multiple diseases.

In the information processing apparatus, when a certainty factor of each of diseases obtained through inference is larger than a certain threshold, the inference unit may acquire such diseases as one or more candidate diseases. By binarizing the certainty factor of each disease using a certain threshold, a consistent determination can be made on the certainty factor.

In the information processing apparatus, the threshold may be set for each disease, for a group including a plurality of diseases, or for a combination of each disease and the group. Compared to when a same threshold is used for all diseases, when a threshold is set for each disease, the threshold can be set finely according to characteristics of the disease, such as whether the disease is relatively easy to detect or whether early detection is highly important for the disease. For example, by grouping diseases with small numbers of incidences, it is possible to indicate with high accuracy that there can be some diseases although names of individual candidate diseases cannot be presented.

In the information processing apparatus, the threshold may be set so as to maximize a certain evaluation criterion for the certainty factor of each of the diseases obtained through inference. The present aspect can minimize differences between an environment in which learning data has been collected and an environment in which inferences are actually made.

In the information processing apparatus, the threshold may be set so as to maximize prediction accuracy of the inference unit, the prediction accuracy being evaluated by k-fold cross-validation of learning data used in generating the first learned model. The present aspect makes it possible to accurately evaluate the prediction accuracy and set such a threshold that maximizes the prediction accuracy even when data during inference cannot be acquired.

A method according to another aspect of the present disclosure comprises: acquiring a medical image; extracting one or more image feature values from the medical image; inferring one or more diseases predicted from the medical image, based on the one or more image feature values and a classification basis, the classification basis being a set of basis vectors that represent correlations between each of the diseases and other diseases by using a vector of a certain dimension; and outputting inferred results.

A computer-readable recording medium according to another aspect of the present disclosure records a program that causes one or more computers to perform the processes of: acquiring a medical image; extracting an one or more image feature values from the medical image; inferring one or more diseases predicted from the medical image, based on the one or more image feature values and a classification basis, the classification basis being a set of basis vectors that represent correlations between each of the diseases and other diseases by using a vector of a certain dimension; and outputting inferred results.

An information processing apparatus according to another aspect of the present disclosure comprises: a first machine learning model that outputs one or more image feature values from an image, the image feature value representing a feature of the image; a second machine learning model that outputs a classification basis that has learned correlations among diseases from input data generated based on label information about a plurality of medical images labeled with one or more diseases; a learning unit that causes the first machine learning model and the second machine learning model to do learning using the plurality of medical images labeled with one or more diseases, find certainty factors of the respective diseases based on the one or more image feature values acquired from the first machine learning model and the classification basis acquired from the second machine learning model, and cause the first machine learning model and the second machine learning model to do learning so as to minimize differences between the certainty factors and the diseases labeled to the medical images, the classification basis being a set of basis vectors that represent correlations between each of the diseases and other diseases by using a vector of a certain dimension; a model output unit that outputs a learned model obtained through learning done by the first machine learning model; and a basis output unit that outputs the classification basis obtained through learning done by the second machine learning model.

The present aspect provides the image feature extraction unit that can be used to infer a disease predicted from a medical image and the classification basis that has learned correlations among diseases.

A method according to another aspect of the present disclosure comprises: acquiring a plurality of medical images labeled with one or more diseases and a plurality of medical images free of diseases; causing a first machine learning model and a second machine learning model to do learning using the medical images, where the first machine learning model being a machine learning model that outputs one or more image feature values from an image, the image feature value representing a feature of the image, the second machine learning model being a machine learning model that outputs a classification basis that has learned correlations among diseases from input data generated based on label information about the plurality of medical images labeled with one or more diseases, finding certainty factors of the respective diseases based on the one or more image feature values acquired from the first machine learning model and the classification basis acquired from the second machine learning model, and causing the first machine learning model and the second machine learning model to do learning so as to minimize differences between the certainty factors and the diseases labeled to the medical images, the classification basis being a set of basis vectors that represent correlations between each of the diseases and other diseases by using a vector of a certain dimension; outputting a learned model obtained through learning done by the first machine learning model; and outputting the classification basis obtained through learning done by the second machine learning model.

Advantageous Effects of Invention

The present disclosure can provide an information processing apparatus, an information processing method, and a computer-readable recording medium that can infer one or more diseases from a medical image.

DESCRIPTION OF EMBODIMENTS

Embodiments of the present invention will be described with reference to the accompanying drawings. Note that the embodiments described below are intended to facilitate the understanding of the present invention, but are not to be interpreted as limiting the present invention. Also, various changes can be made to the present invention without departing from the gist of the present invention. Furthermore, those skilled in the art can adopt embodiments obtained by replacing elements described below with equivalents and such embodiments are also included in the scope of the present invention.

(System Configuration)

Figure 1:
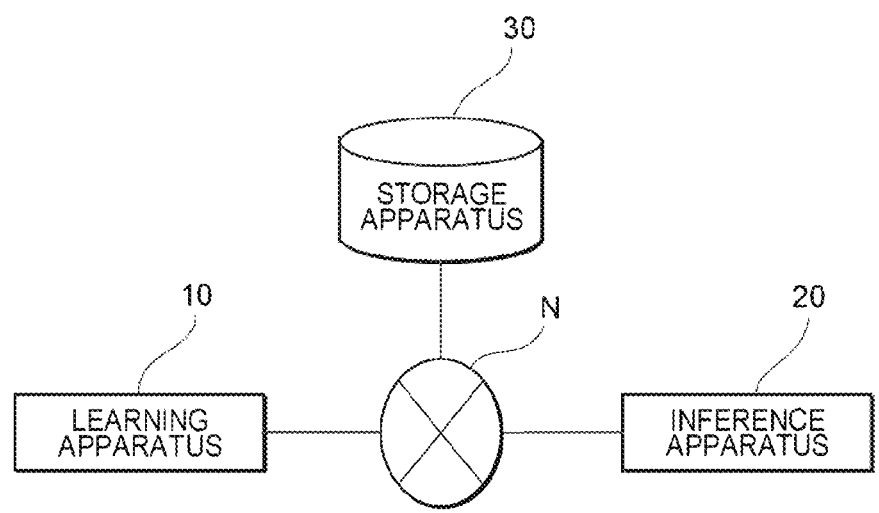
FIG. 1 is a diagram showing a network configuration of an information processing system according to one embodiment.
Figure 2:
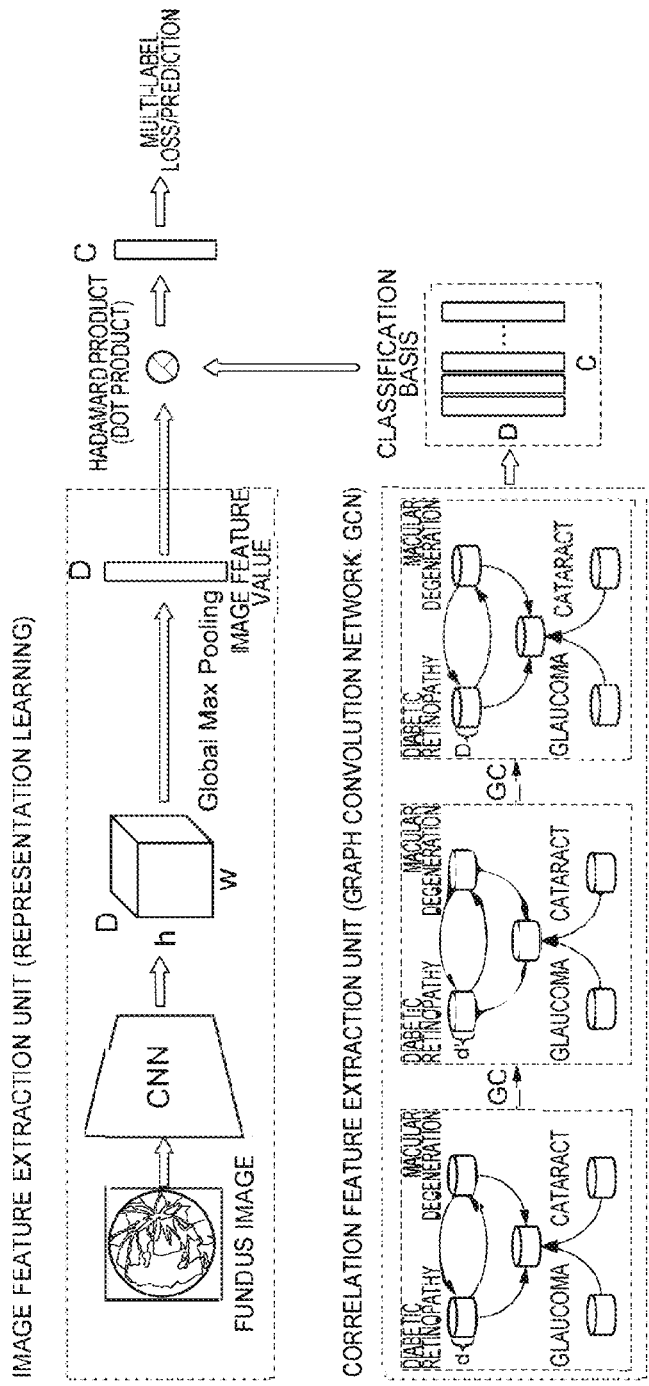
FIG. 2 is a schematic diagram showing processes of a learning apparatus according to one embodiment.
Figure 3:
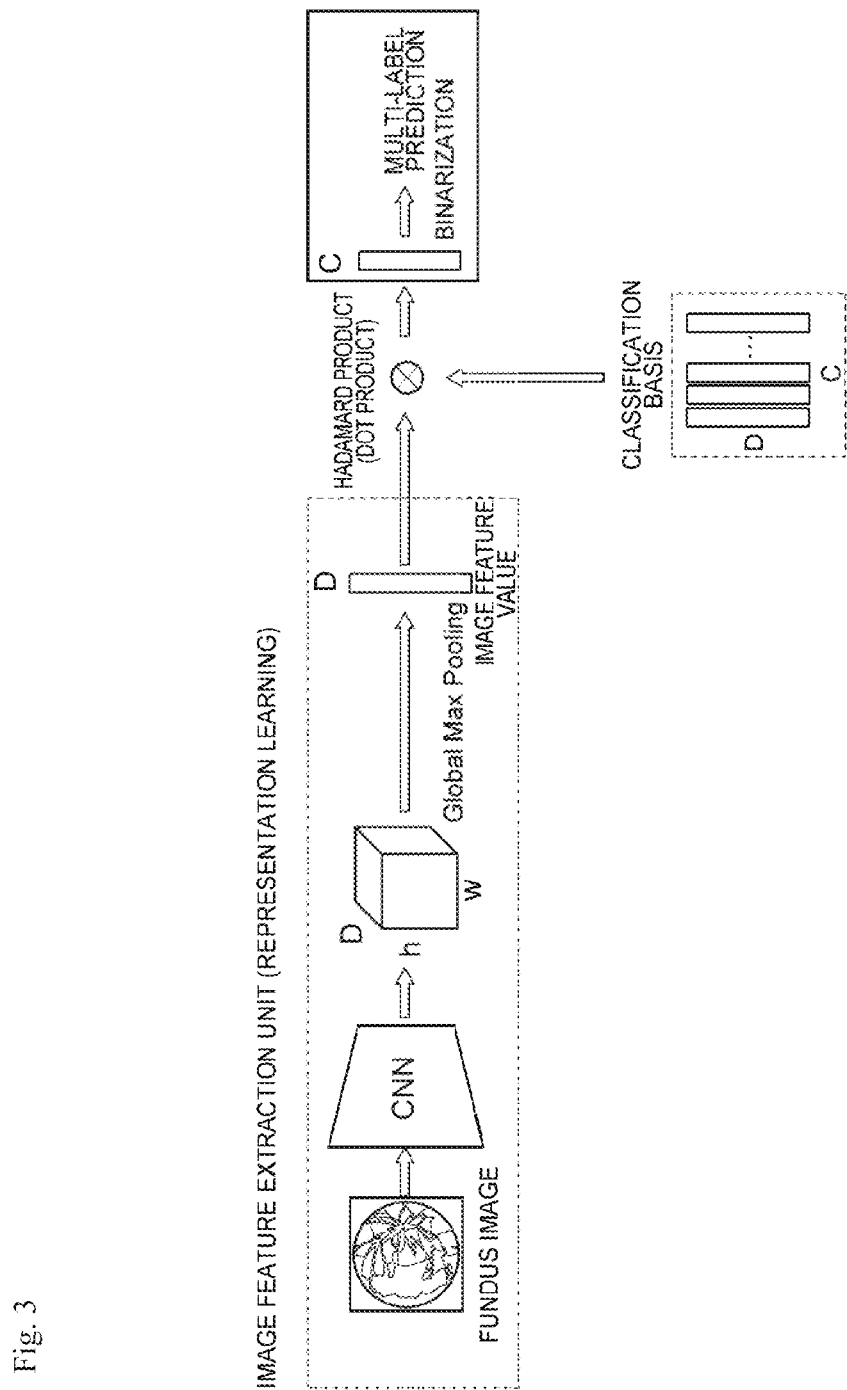
FIG. 3 is a schematic diagram showing processes of an inference apparatus according to one embodiment.

The present disclosure will be outlined with reference to FIGS. 1, 2, and 3. FIG. 1 is a diagram showing a network configuration of an information processing system according to one embodiment. FIG. 2 is a schematic diagram showing processes of a learning apparatus according to one embodiment. FIG. 3 is a schematic diagram showing processes of an inference apparatus according to one embodiment.

The information processing system includes a learning apparatus 10, an inference apparatus 20, and a storage apparatus 30. The learning apparatus 10 is connected to the inference apparatus 20 and the storage apparatus 30 via a communications network N. The communications network N may be either a wired communications network or a wireless communications network made up of a wired or wireless circuit, or the Internet or a local area network (LAN).

The learning apparatus 10 causes machine learning models to do learning based on learning data stored in the storage apparatus 30 and stores learned models in the storage apparatus 30. Although the learning apparatus 10 according to the present embodiment includes the machine learning models, the machine learning models may be provided separately from the learning apparatus 10.

Here, the machine learning model has a certain model structure and process parameters that change with a learning process and has its identification accuracy improved when the process parameters are optimized based on experience obtained from learning data. That is, the machine learning model learns optimum process parameters through a learning process. Regarding algorithms for the machine learning model, for example, Support Vector Machine, Logistic Regression, and Neural Network are available for use, but the type of neural network is not specifically limited. Some of the machine learning models that undergo the learning have not undergone any learning yet, and the others have already undergone some learning using learning data.

Note that the learned model is a model that has done learning in advance using appropriate learning data in contrast to the machine learning model that does learning based on any machine learning algorithm. However, it is not that the learned model no longer does any more learning and the learned model can do additional learning.

The inference apparatus 20 outputs output data corresponding to characteristics of input data using a learned model. The inference apparatus 20 according to the present embodiment makes inferences using a learned model acquired from the storage apparatus 30. Here, acquiring a learned model means acquiring information needed to reproduce functions of the learned model on the inference apparatus 20. For example, when a neural network is used as a machine learning model, acquiring a learned model means acquiring at least information about the number of layers in the neural network, the number of nodes in each layer, weight parameters of links interconnecting the nodes, bias parameters of the respective nodes, and function forms of activation functions of the respective nodes.

The storage apparatus 30 stores learning data used for learning done by the machine learning model. The storage apparatus 30 according to the present embodiment stores fundus images labeled with one or more retinal diseases and fundus images free of retinal diseases as learning data. The storage apparatus 30 also stores learned models outputted by the learning apparatus 10. Although shown as a single storage apparatus in FIG. 1, the storage apparatus 30 may be made up of one or more file servers. Although in the present embodiment, a fundus image labeled with one or more retinal diseases is used as an example of learning data, according to another embodiment, a medical image labeled with one or more diseases in another examination region of a patient may be used as learning data.

As shown in FIG. 2, the learning apparatus 10 according to the present embodiment includes a machine learning model (first machine learning model) that outputs one or more image feature values from a fundus image, the image feature value representing a feature of the a fundus image, and a machine learning model (second machine learning model) that outputs a classification basis that has learned correlations among retinal diseases from input data generated based on label information about a plurality of fundus images labeled with one or more retinal diseases. The classification basis is a set of basis vectors that represent correlations between each of the diseases and other diseases by using a vector of a certain dimension.

Using the one or more image feature values outputted from the first machine learning model and the classification basis outputted from the second machine learning model, the learning apparatus 10 predicts a retinal disease from fundus images and causes the first machine learning model and the second machine learning model to do learning so as to minimize differences between predicted results and retinal diseases labeled to learning data. Although in the present embodiment, description is given of a case in which fundus images, which are an example of medical images, are used, according to another embodiment, chest images, brain images, liver images, or the like acquired by photographing another examination region of a patient may be used.

By causing the machine learning models to learn not only information from fundus images, but also correlations among diseases, it is possible to generate learned models that enable high-accuracy inferences that take the correlations among diseases into account.

As shown in FIG. 3, using the learned model obtained through learning done by the first machine learning model and the classification basis obtained through learning done by the second machine learning model, the inference apparatus 20 according to the present embodiment infers retinal diseases predicted from a fundus image. By using the classification basis that has learned correlations among diseases in inferring diseases, the inference can be made with higher accuracy than when the inference is made using only a fundus image. Furthermore, the inference apparatus 20 according to the present embodiment can present multiple disease candidates using a single fundus image without generating learned models corresponding to respective diseases. Although in the present embodiment, disease candidates are inferred from a fundus image, which is an example of a medical image, according to another embodiment, diseases can be inferred using medical images such as chest images, brain images, liver images, or the like acquired by photographing another examination region of a patient.

(Functional Configuration: Learning Apparatus)

Figure 4:
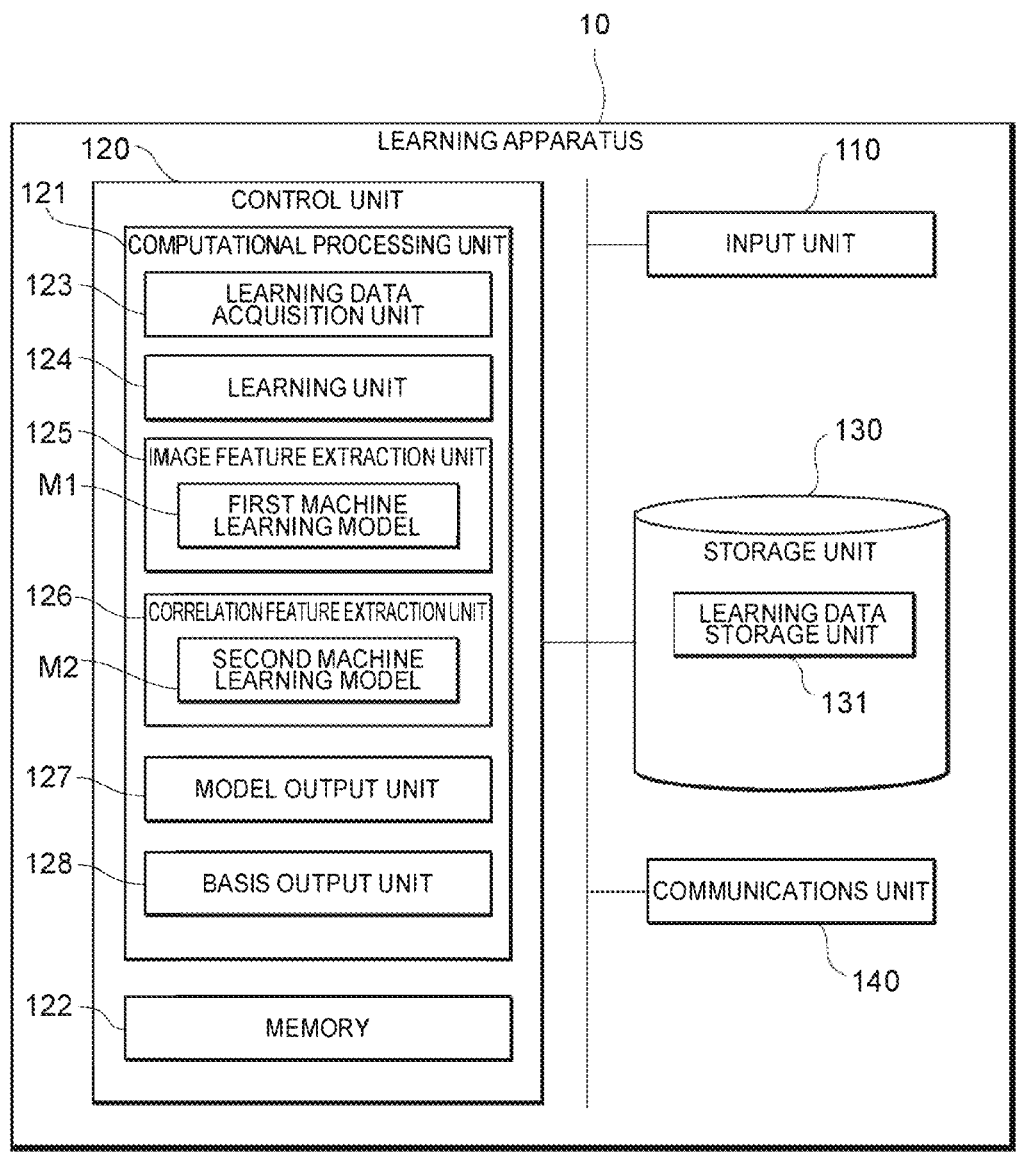
FIG. 4 is a block diagram of the learning apparatus according to one embodiment.

FIG. 4 is a block diagram of the learning apparatus according to one embodiment. Note that only necessary functional components are shown in FIG. 4 by assuming a single learning apparatus 10, but the learning apparatus 10 may be configured as part of a multi-functional distributed system made up of multiple computer systems.

The learning apparatus 10 includes an input unit 110, a control unit 120, a storage unit 130, and a communications unit 140.

The input unit 110, which is configured to accept operations from an administrator of the learning apparatus 10, can be implemented by a keyboard, a mouse, a touch panel, and the like.

The control unit 120 includes a computational processing unit 121, such as a CPU or an MPU, which corresponds to a processor, and a memory 122 such as a RAM. Based on various types of input, the computational processing unit 121 (processor) executes a program stored in the storage unit 130 by loading the program into the memory 122 and thereby implements after-mentioned functions and processes of the computational processing unit 121. The program may be installed on a computer by being stored in a non-transitory computer-readable recording medium such as a CD-ROM or by being distributed through a network. The memory 122 functions as working memory needed by the computational processing unit 121 (processor) in order to execute the program.

The storage unit 130, which is made up of a storage apparatus such as a hard disk, records various programs needed by the control unit 120 in order to perform processes as well as data and the like necessary for execution of the various programs. In the present embodiment, desirably the storage unit 130 includes a learning data storage unit 131.

The learning data storage unit 131 stores learning data used for learning done by a first machine learning model M1 and a second machine learning model M2 described later. According to the present embodiment, the learning data storage unit 131 stores fundus images labeled with one or more retinal diseases and fundus images free of retinal diseases.

The communications unit 140 is configured to connect the learning apparatus 10 to a network. For example, the communications unit 140 can be implemented by a LAN card, an analog modem, an ISDN modem, or the like as well as an interface for use to connect these devices to a processing unit via a transmission path such as a system bus.

Furthermore, as shown in FIG. 4, the computational processing unit 121 includes, as functional components, a learning data acquisition unit 123, a learning unit 124, an image feature extraction unit 125, a correlation feature extraction unit 126, a model output unit 127, and a basis output unit 128.

The learning data acquisition unit 123 acquires learning data used for learning done by the first machine learning model M1 and the second machine learning model M2 described later, and stores the learning data in the learning data storage unit 131. According to the present embodiment, the learning data acquisition unit 123 acquires a fundus image labeled with one or more retinal diseases and a fundus image free of retinal diseases from the storage apparatus 30 and stores the fundus images in the learning data storage unit 131.

Using the learning data acquired by the learning data acquisition unit 123, the learning unit 124 causes the first machine learning model M1 and the second machine learning model M2 to do learning. According to the present embodiment, as shown in FIG. 2, first the learning unit 124 inputs the fundus image labeled with one or more retinal diseases and the fundus image free of retinal diseases to the after-mentioned image feature extraction unit 125 and correlation feature extraction unit 126, respectively, and acquires a classification basis regarding correlations between one or more image feature values extracted from the fundus image and retinal diseases extracted from the label information.

Next, the learning unit 124 finds the Hadamard product of the one or more image feature values acquired from the image feature extraction unit 125 and the classification basis acquired from the correlation feature extraction unit 126, applies an activation function to the Hadamard product, and causes the first machine learning model M1 and the second machine learning model M2 to do learning so as to minimize differences between certainty factors of resulting C retinal diseases and retinal diseases labeled to the learning data. Here, C is the number of retinal diseases to be predicted and is equal to the number of vectors making up the classification basis as described later.

The image feature extraction unit 125 accepts input of an image and extracts one or more image feature values, each represents a feature of the image, from the image. According to the present embodiment, the image feature extraction unit 125 accepts a fundus image as input and extracts one or more image feature values from the fundus image using the first machine learning model M1.

The first machine learning model M1 is a machine learning model that outputs one or more image feature values from an image, where the image feature value represents a feature of the image. In the present embodiment, a description will be given of an example that uses, as an example of the first machine learning model M1, a convolutional neural network (CNN) that accepts a fundus image as input data and outputs one or more image feature values, where the image feature value represents a feature of the fundus image. However, the CNN is only an example of the first machine learning model M1, and the learning apparatus 10 may use a learning model of another configuration as the first machine learning model M1.

According to one embodiment, the first machine learning model M1 applies global max pooling (GMP) in a final convolutional layer and outputs a D-dimensional image feature values. Such application of GMP that selects a maximum value on each channel of a feature map enables effective down-sampling, leaving important image feature values.

The correlation feature extraction unit 126 extracts a classification basis regarding correlations among diseases from multiple images labeled with one or more diseases. The classification basis is a set of basis vectors that represent correlations between each of the diseases and other diseases by using a vector of a certain dimension. For example, as shown in FIG. 2, according to the present embodiment, the classification basis is represented as a set of basis vectors that represent correlations between the C diseases and other diseases by using a D-dimensional vector.

According to the present embodiment, the correlation feature extraction unit 126 accepts input of a fundus image labeled with one or more retinal diseases, generates graph data embedded with label information about the fundus image as data in multi-hot vector form, and extracts a classification basis using the second machine learning model M2. As shown in FIG. 2, each node of the graph data corresponds to a retinal disease. Although in FIG. 2, the graph data is shown in a simplified form, it is assumed that graph data having C nodes corresponding to C retinal diseases is generated.

The second machine learning model M2 outputs a feature that has learned correlations among items to be learned. In the present embodiment, a description will be given of an example that uses, as an example of the second machine learning model M2, a graph convolutional neural network (GCN) that accepts graph data generated by the correlation feature extraction unit 126 as input data, and outputs a classification basis that has learned correlations among retinal diseases. However, the GCN is only an example of the second machine learning model M2, and the learning apparatus 10 may use a learning model of another configuration as the second machine learning model M2. In the present embodiment, the second machine learning model M2 represents the feature values of nodes by using the d-th dimension, convolves information about adjacent nodes with the feature value of each node according to adjacent relationships in a graph, and outputs a D-dimensional classification basis.

When the first machine learning model M1 and the second machine learning model M2 finish learning, the model output unit 127 outputs a learned model obtained as a result of the learning done by the first machine learning model M1 to the storage apparatus 30. Note that the learning unit 124 may complete learning, for example, after making the first machine learning model M1 and the second machine learning model M2 learn a certain number of learning data or when accuracy of retinal diseases predicted by the first machine learning model M1 and the second machine learning model M2 satisfies certain conditions.

Similarly, when the first machine learning model M1 and the second machine learning model M2 finish learning, the basis output unit 128 outputs a classification basis obtained as a result of the learning done by the second machine learning model M2 to the storage apparatus 30.

(Functional Configuration: Inference Apparatus)

Figure 5:
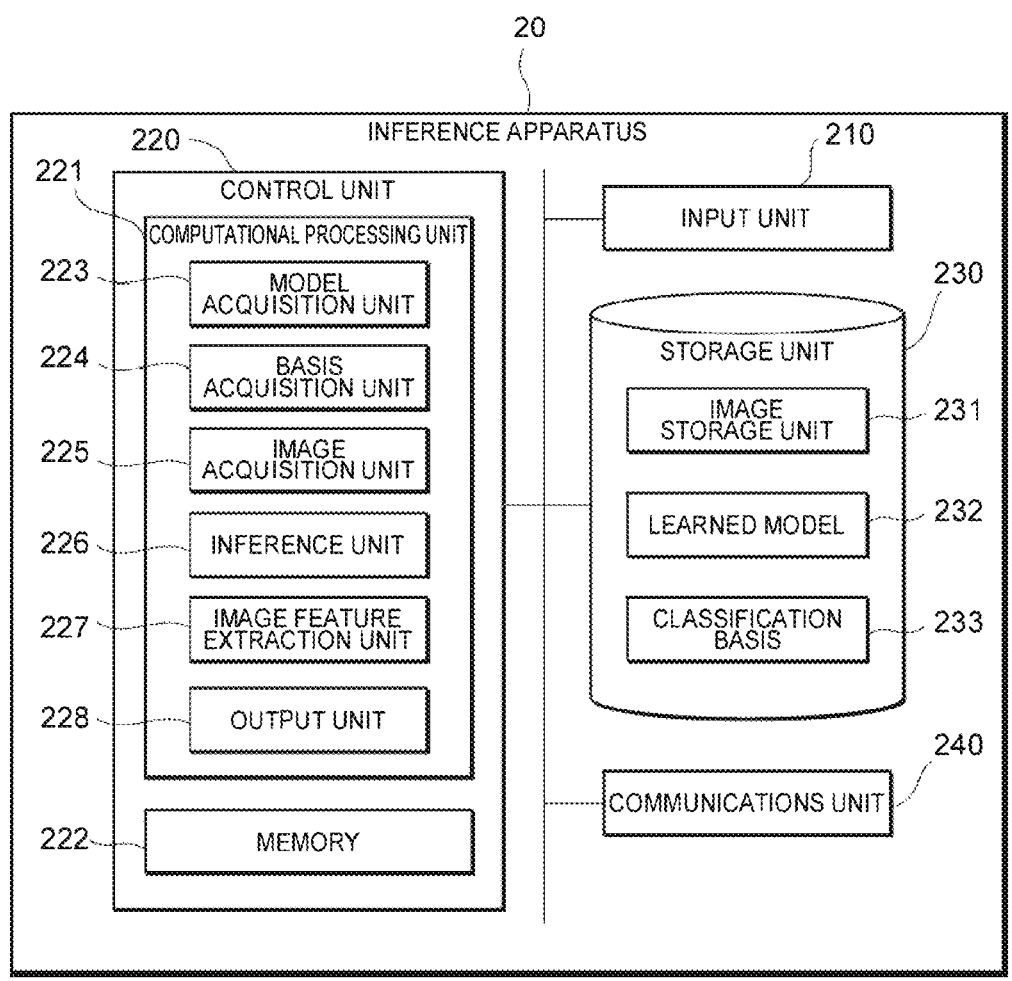
FIG. 5 is a block diagram of the inference apparatus according to one embodiment.

FIG. 5 is a block diagram of the inference apparatus according to one embodiment. Note that only necessary functional components are shown in FIG. 5 by assuming a single inference apparatus 20, but the inference apparatus 20 may be configured as part of a multi-functional distributed system made up of multiple computer systems.

The inference apparatus 20 includes an input unit 210, a control unit 220, a storage unit 230, and a communications unit 240.

The input unit 210, which is configured to accept operations from an administrator of the inference apparatus 20, can be implemented by a keyboard, a mouse, a touch panel, and the like.

The control unit 220 includes a computational processing unit 221, such as a CPU or an MPU, which corresponds to a processor, and a memory 222 such as a RAM. Based on various types of input, the computational processing unit 221 (processor) executes a program stored in the storage unit 230 by loading the program into the memory 222 and thereby implements after-mentioned functions and processes of the computational processing unit 221. The program may be installed on a computer by being stored in a non-transitory computer-readable recording medium such as a CD-ROM or by being distributed through a network. The memory 222 functions as working memory needed by the computational processing unit 221 (processor) in order to execute the program.

The storage unit 230, which is made up of a storage apparatus such as a hard disk, records various programs needed by the control unit 220 in order to perform processes as well as data and the like necessary for execution of the various programs. According to the present embodiment, desirably the storage unit 230 includes an image storage unit 231, a learned model 232, and a classification basis 233.

The image storage unit 231 stores images to be used for inference. According to the present embodiment, the image storage unit 231 stores fundus images from which retinal diseases are inferred.

The learned model 232 stores learned models used for inference. According to the present embodiment, the learned model 232 stores learned models that accept fundus images as input data and output image feature values that represent features of the fundus images. In the present embodiment, a description will be given of an example that uses, as an example of the learned model 232, a convolutional neural network (CNN) that accepts a fundus image as input data, and outputs one or more image feature values, where the image feature value represents a feature of the fundus image. However, the CNN is only an example of the learned model 232, and the inference apparatus 20 may use a learned model database of another configuration as the learned model 232.

The classification basis 233 stores basis vectors used for inference. According to the present embodiment, the classification basis 233 stores a set of basis vectors that represent correlations between each disease and other diseases by using a vector of a certain dimension.

The communications unit 240 is configured to connect the inference apparatus 20 to a network. For example, the communications unit 240 can be implemented by a LAN card, an analog modem, an ISDN modem, or the like as well as an interface for use to connect these devices to a processing unit via a transmission path such as a system bus.

Furthermore, as shown in FIG. 5, the computational processing unit 221 includes, as functional components, a model acquisition unit 223, a basis acquisition unit 224, an image acquisition unit 225, an inference unit 226, an image feature extraction unit 227, and an output unit 228.

The model acquisition unit 223 acquires learned models used for inference and stores the learned models in the learned model 232. According to the present embodiment, the model acquisition unit 223 acquires learned models from the storage apparatus 30 and stores the learned models in the learned model 232.

The basis acquisition unit 224 acquires basis vectors used for inference and stores the basis vectors in the classification basis 233. According to the present embodiment, the basis acquisition unit 224 acquires classification bases from the storage apparatus 30 and stores the classification bases in the classification basis 233.

The image acquisition unit 225 acquires images to be used for inference. According to the present embodiment, the image acquisition unit 225 acquires fundus images for use to infer retinal diseases, from the image storage unit 231.

The inference unit 226 infers retinal diseases predicted from the image acquired by the image acquisition unit 225. According to the present embodiment, as shown in FIG. 3, first the inference unit 226 acquires one or more image feature values by inputting the fundus image acquired by the image acquisition unit 225 to the image feature extraction unit 227 described later, and finds the Hadamard product of the acquired one or more image feature values and the classification basis 233. Next, using a certain threshold, the inference unit 226 binarizes the respective certainty factors of the C retinal diseases obtained by the application of an activation function to the Hadamard product, and acquires retinal diseases having certainty factors larger than the certain threshold, as candidate diseases. According to one embodiment, in addition to or instead of information about the candidate diseases, the inference unit 226 may hand over the respective certainty factors of the C retinal diseases obtained by the application of the activation function to the Hadamard product to the output unit 228.

Here, the threshold used to determine the candidate diseases may be a value set in advance or a value entered by the administrator via the input unit 210. For example, by setting three thresholds in advance according to characteristics of facilities that use the inference apparatus 20, one of the thresholds may be set according to input from the administrator. Facilities that carry out medical examination can use a low threshold to widely point out possible diseases, general facilities that carry out diagnosis and treatment can use a central threshold to point out diseases potentially subject to treatment, and special facilities that provide advanced medical care can use a high threshold to point out diseases potentially subject to advanced medical care. Furthermore, the thresholds set in advance may be allowed to be adjusted according to input from the administrator. If thresholds are made adjustable, more optimized inference results can be outputted according to classes of patients or policies of facilities.

According to one embodiment, the inference unit 226 may set a threshold for each retinal disease or for a group of multiple retinal diseases. Compared to when a same threshold is set for all diseases, if a threshold is set for each disease, the threshold can be set finely according to characteristics of the disease such as whether the disease is relatively easy to find or whether early detection is of great importance for the disease. On the other hand, for example, it is difficult to set an appropriate threshold individually for every one of more than 100 types of retinal disease, and when a case in which one lesion appears as a result of more than two diseases is considered, it is practically impossible to set an appropriate threshold for each retinal disease. In such a case, if individual thresholds for respective retinal diseases and a threshold for a group of multiple retinal diseases are used in combination, candidate diseases can be acquired accurately. That is, by grouping diseases with small numbers of incidences, it is possible to show accurately that some disease may exist although no individual candidate disease name can be presented.

The image feature extraction unit 227 accepts input of an image and extracts one or more image feature values, each represents a feature of the image, from the image. According to the present embodiment, the image feature extraction unit 227 accepts a fundus image as input and extracts one or more image feature values from the fundus image using the learned model 232.

The output unit 228 outputs inference results that are based on information acquired by the inference unit 226. According to the present embodiment, the output unit 228 outputs inference results that are based on information about candidate diseases acquired by the inference unit 226. According to one embodiment, the output unit 228 may output the certainty factors of diseases in addition to or instead of information about the candidate diseases.

First Embodiment (Learning Process)

Figure 6:
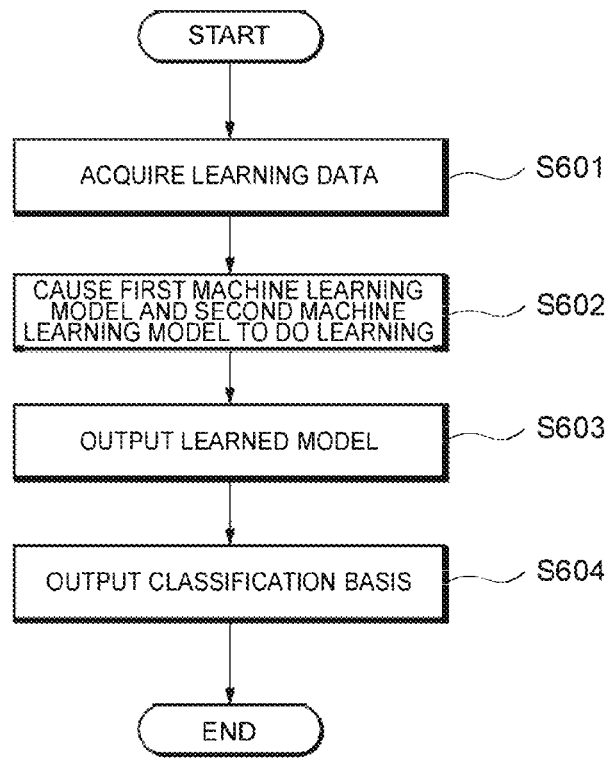
FIG. 6 is a flowchart showing a learning process of the learning apparatus according to one embodiment.

A learning process of the learning apparatus according to one embodiment will be described in detail with reference to FIG. 6. According to the present embodiment, it is assumed that before the learning process described in FIG. 6 is performed, learning data is stored in the storage apparatus 30 under the supervision of the administrator of the learning apparatus 10. Note that the process shown in FIG. 6 is performed, for example, when the administrator enters a command via the input unit 110 to perform the process of generating a learned model.

In step S601, the learning data acquisition unit 123 of the learning apparatus 10 acquires learning data used for learning done by the first machine learning model M1 and the second machine learning model M2 and stores the learning data in the learning data storage unit 131. According to the present embodiment, the learning data acquisition unit 123 acquires a fundus image labeled with one or more retinal diseases and a fundus image free of retinal diseases from the storage apparatus 30 and stores the fundus images in the learning data storage unit 131.

Next, in step S602, using the learning data acquired by the learning data acquisition unit 123, the learning unit 124 of the learning apparatus 10 causes the first machine learning model M1 and the second machine learning model M2 to do learning.

The first machine learning model M1 outputs one or more image feature values from an image, where the image feature value represents a feature of the image. In the present embodiment, a convolutional neural network (CNN) that accepts a fundus image as input data and outputs one or more image feature values, where the image feature value represents a feature of the fundus image is used as an example of the first machine learning model M1. However, the CNN is only an example of the first machine learning model M1, and the learning apparatus 10 may use a learning model of another configuration as the first machine learning model M1.

Furthermore, according to the present embodiment, as shown in FIG. 2, the first machine learning model M1 applies global max pooling (GMP) in a final convolutional layer and outputs a D-dimensional image feature values. Such application of GMP that selects a maximum value on each channel of a feature map enables effective downsampling, leaving important image feature values.

The second machine learning model M2 outputs a feature that has learned correlations among items to be learned. In the present embodiment, a graph convolutional neural network (GCN) that accepts graph data as input data and outputs a classification basis that has learned correlations among retinal diseases is used as an example of the second machine learning model M2. However, the GCN is only an example of the second machine learning model M2, and the learning apparatus 10 may use a learning model of another configuration as the second machine learning model M2. In the present embodiment, the second machine learning model M2 represents the feature values of nodes by using the d-th dimension, convolves information about adjacent nodes with the feature value of each node according to adjacent relationships in a graph, and outputs a D-dimensional classification basis.

Specifically, according to the present embodiment, the learning unit 124 inputs a fundus image labeled with one or more retinal diseases and a fundus image free of retinal diseases to the image feature extraction unit 125 and the correlation feature extraction unit 126, respectively. The image feature extraction unit 125 of the learning apparatus 10 accepts the fundus images as input and extracts image feature values from the fundus images using the first machine learning model M1. The correlation feature extraction unit 126 of the learning apparatus 10 accepts input of the fundus image labeled with one or more retinal diseases, generates graph data embedded with label information about the fundus image as data in multi-hot vector form, and extracts a classification basis using the second machine learning model M2. According to the present embodiment, as shown in FIG. 2, the correlation feature extraction unit 126 generates graph data having C nodes corresponding to C retinal diseases, and using the second machine learning model M2, extracts the classification basis, which is a set of basis vectors that represent correlations between the C diseases and other diseases by using a D-dimensional vector.

When the processes of the image feature extraction unit 125 and the correlation feature extraction unit 126 are finished, the learning unit 124 finds the Hadamard product of the one or more image feature values acquired from the image feature extraction unit 125 and the classification basis acquired from the correlation feature extraction unit 126, applies an activation function to the Hadamard product, and causes the first machine learning model M1 and the second machine learning model M2 to do learning so as to minimize differences between certainty factors of resulting C retinal diseases and retinal diseases labeled to the learning data.

When the first machine learning model M1 and the second machine learning model M2 finish learning, in step S603, the model output unit 127 of the learning apparatus 10 outputs the learned model obtained as a result of the learning done by the first machine learning model M1 to the storage apparatus 30. Note that the learning unit 124 may complete learning, for example, after making the first machine learning model M1 and the second machine learning model M2 learn a certain number of learning data or when accuracy of retinal diseases predicted by the first machine learning model M1 and the second machine learning model M2 satisfies certain conditions.

Similarly, when the first machine learning model M1 and the second machine learning model M2 complete learning, in step S604, the basis output unit 128 of the learning apparatus 10 outputs the classification basis obtained as a result of the learning done by the second machine learning model M2 to the storage apparatus 30.

(Inference Process)

Figure 7:
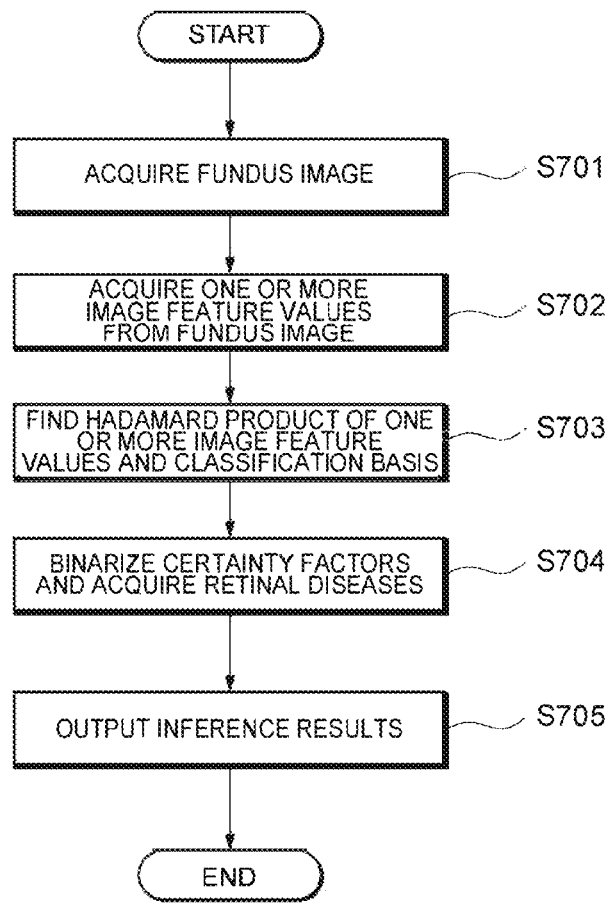
FIG. 7 is a flowchart showing an inference process of the inference apparatus according to one embodiment.

An inference process of the inference apparatus according to one embodiment will be described in detail with reference to FIG. 7. According to the present embodiment, it is assumed that before the inference process described in FIG. 7 is performed, a learned model and a classification basis acquired from the storage apparatus 30 are stored in the learned model 232 and the classification basis 233 under the supervision of the administrator of the inference apparatus 20. It is also assumed that a fundus image to be used for inference is stored in the image storage unit 231 of the inference apparatus 20. Note that the process shown in FIG. 7 is performed, for example, when the administrator enters a command via the input unit 210 to perform the inference process.

In step S701, the image acquisition unit 225 of the inference apparatus 20 acquires the image to be used for inference. According to the present embodiment, the image acquisition unit 225 acquires a fundus image to be used for inference of retinal diseases, from the image storage unit 231.

In step S702, the inference unit 226 of the inference apparatus 20 inputs the fundus image acquired by the image acquisition unit 225 to the image feature extraction unit 227 and thereby acquires one or more image feature values. Specifically, the image feature extraction unit 227 accepts input of the fundus image and extracts the one or more image feature values from the fundus image using the learned model 232.

In the present embodiment, a convolutional neural network (CNN) that accepts a fundus image as input data and outputs one or more image feature values, where the image feature value represents a feature of the fundus image is used as an example of the learned model 232. As shown in FIG. 3, the learned model 232 used here applies global max pooling (GMP) in a final convolutional layer and outputs a D-dimensional image feature values. Such application of GMP that selects a maximum value on each channel of a feature map enables effective down-sampling, leaving important image feature values.

Next, in step S703, the inference unit 226 finds the Hadamard product of the acquired one or more image feature values and the classification basis 233.

Finally, in step S704, using a certain threshold, the inference unit 226 binarizes the respective certainty factors of the C retinal diseases obtained by the application of an activation function to the Hadamard product, and acquires retinal diseases having certainty factors larger than the certain threshold, as candidate diseases. According to one embodiment, in addition to or instead of information about the candidate diseases, the inference unit 226 may hand over the respective certainty factors of the C retinal diseases obtained by the application of the activation function to the Hadamard product to the output unit 228.

In step S705, the output unit 228 of the inference apparatus 20 outputs inference results that are based on information acquired by the inference unit 226. According to the present embodiment, the output unit 228 outputs inference results that are based on information about candidate diseases acquired by the inference unit 226. According to one embodiment, the output unit 228 may output the certainty factors of diseases in addition to or instead of information about the candidate diseases.

In the present embodiment, description has been given of an example in which the correlation feature extraction unit 126 generates graph data having nodes corresponding to retinal diseases. According to one embodiment, in addition to retinal diseases, the correlation feature extraction unit 126 may generate graph data having nodes corresponding to lesions related to diseases such as an abnormal blood circulation area or a tissue degeneration area including a non-perfusion area in which no blood or almost no blood flows. This will make it possible to infer not only retinal diseases, but also lesions related to retinal diseases, from a fundus image, find the certainty factors of the diseases, and present inference results. Consequently, the doctor can work out a treatment strategy by taking into account, for example, information about lesions and the like common to multiple diseases.

Thus, according to the present embodiment, the learning apparatus 10 includes the image feature extraction unit 227 that can be used for inference of retinal diseases predicted from a fundus image, and a classification basis that has learned correlations among retinal diseases.

According to the present embodiment, using the classification basis that has learned correlations among retinal diseases for inference of retinal diseases, the inference apparatus 20 allows one or more retinal diseases to be inferred among a wide variety of retinal diseases. Besides, by using the classification basis, the present embodiment can utilize information about correlations among diseases not utilized conventionally, and consequently, can make inference with higher accuracy than when the inference is made using only a fundus image.

Second Embodiment

In relation to the learning process and inference process described above, in S704 of the inference process, description has been given of an example in which the same threshold is used for all diseases. In the present embodiment, description will be given of an example in which individual thresholds for respective retinal diseases and a threshold for a group of multiple retinal diseases are used in combination in S704 of the inference process. Here, the inference unit 226 uses thresholds of 50%, 20%, and 20% set separately for glaucoma, age-related macular degeneration, and diabetic retinopathy. Regarding other retinal diseases, the inference unit 226 uses a threshold of 10% set for a group of the other retinal diseases.

(Learning Process)

In the first embodiment, as shown in FIG. 2, the correlation feature extraction unit 126 generates graph data, each node of which corresponds to C retinal diseases and inputs the graph data to the second machine learning model M2. According to a second embodiment, the correlation feature extraction unit 126 generates graph data corresponding to glaucoma, age-related macular degeneration, diabetic retinopathy, and other retinal diseases and inputs the graph data to the second machine learning model M2. That is, whereas graph data having C nodes corresponding to C retinal diseases is generated in the first embodiment, graph data having four nodes is generated in the second embodiment.

As described above, the second machine learning model M2 is a machine learning model that outputs a feature that has learned correlations among items to be learned. Also in the second embodiment, as with the first embodiment, the second machine learning model M2 represents the feature values of nodes by using the d-th dimension, convolves information about adjacent nodes with the feature value of each node according to adjacent relationship in a graph, and outputs a D-dimensional classification basis.

The learning process described using FIG. 6 is similar to the first embodiment, and thus description thereof will be omitted. Whereas according to the first embodiment, the learning data acquired by the learning data acquisition unit 123 in step S601 is a fundus image labeled with one or more retinal diseases out of C retinal diseases and a fundus image free of retinal diseases, according to the second embodiment, the acquired learning data is a fundus image labeled with one or more retinal diseases out of four retinal diseases—glaucoma, age-related macular degeneration, diabetic retinopathy, and another retinal disease—and a fundus image free of retinal diseases.

(Inference Process)

Of the inference process described using FIG. 7, step S704 different from the first embodiment will be described in detail using FIG. 8.

In step S701, the image acquisition unit 225 acquires the fundus image to be used for inference of retinal diseases, from the image storage unit 231. In step S702, the inference unit 226 of the inference apparatus 20 inputs the fundus image acquired by the image acquisition unit 225 to the image feature extraction unit 227 and thereby acquires one or more image feature values. Specifically, the image feature extraction unit 227 accepts the fundus image as input and extracts one or more image feature values from the fundus image using the learned model 232.

Again, in the second embodiment, a convolutional neural network (CNN) that accepts a fundus image as input data and outputs one or more image feature values, where the image feature value represents a feature of the fundus image is used as an example of the learned model 232. As shown in FIG. 3, the learned model 232 used here applies global max pooling (GMP) in a final convolutional layer and outputs a D-dimensional image feature values. Next, in step S703, the inference unit 226 finds the Hadamard product of the acquired one or more image feature values and the classification basis 233.

In step S704, using a certain threshold, the inference unit 226 binarizes the respective certainty factors of the four retinal diseases obtained by the application of an activation function to the Hadamard product, and acquires retinal diseases having certainty factors larger than the certain threshold, as candidate diseases. According to the present embodiment, the inference unit 226 uses thresholds of 50%, 20%, and 20% set separately for glaucoma, age-related macular degeneration, and diabetic retinopathy. Regarding other retinal diseases, the inference unit 226 uses a threshold of 10% set for a group of the other retinal diseases.

Figure 8:
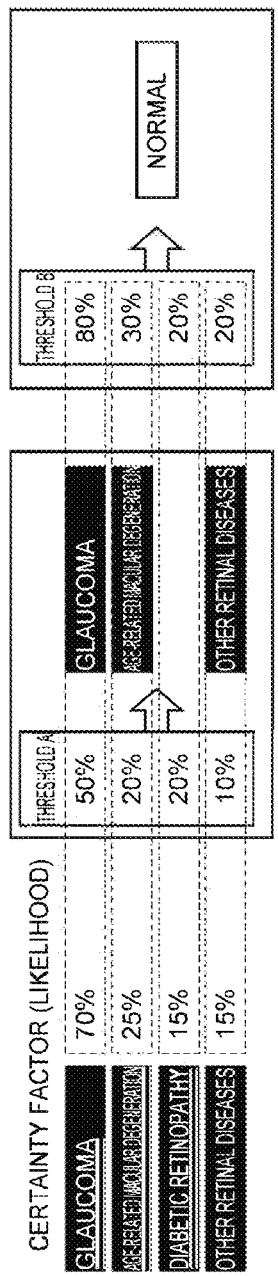
FIG. 8 is a schematic diagram explaining thresholds used by the inference apparatus according to one embodiment.

As shown in the center of FIG. 8, suppose the certainty factors of glaucoma, age-related macular degeneration, diabetic retinopathy, and other retinal diseases predicted from a certain fundus image are 70%, 25%, 15%, and 15%, respectively. In such a case, the inference unit 226 acquires glaucoma, age-related macular degeneration, and other retinal diseases having certainty factors larger than the respective thresholds as candidate diseases.

In step S705, the output unit 228 outputs inference results that are based on information about candidate diseases acquired by the inference unit 226.

As shown on the right side of FIG. 8, if the inference unit 226 uses thresholds of 80%, 30%, and 20% set separately for glaucoma, age-related macular degeneration, and diabetic retinopathy and uses a threshold of 20% set for a group of the other retinal diseases, and if the certainty factors of glaucoma, age-related macular degeneration, diabetic retinopathy, and other retinal diseases predicted from a certain fundus image are 70%, 25%, 15%, and 15%, respectively, because there is no retinal disease having a certainty factor larger than the corresponding threshold, the inference unit 226 hands over information to the output unit 228, indicating that there is no candidate disease.

In this way, even if the certainty factor of a retinal disease predicted from a certain fundus image is the same, if the threshold is allowed to be adjusted, there can be a case in which the retinal disease is presented as a candidate disease and a case in which the retinal disease is not presented as a candidate disease. By optimizing threshold settings, it is possible to output more optimized inference results according to classes of patients or policies of facilities.

Thus, according to the present embodiment, compared to when the same threshold is used for all diseases, if a threshold is set for each disease, the inference apparatus 20 allows the threshold to be set finely according to characteristics of the disease such as whether the disease is relatively easy to find or whether early detection is of great importance for the disease. On the other hand, a threshold for a group of multiple retinal diseases, if used in combination with individual thresholds for respective retinal diseases, allows candidate diseases to be acquired accurately. That is, by grouping diseases with small numbers of incidences, it is possible to show accurately that some disease may exist although no individual candidate disease name can be presented.

(Optimization of Thresholds)

As described thus far, according to one embodiment, the inference apparatus 20 binarizes the respective certainty factors of the C retinal diseases using a certain threshold, and acquires retinal diseases having certainty factors larger than the certain threshold, as candidate diseases. The process enclosed by a solid line in FIG. 3 will be described in detail using FIG. 9.

Figure 9:
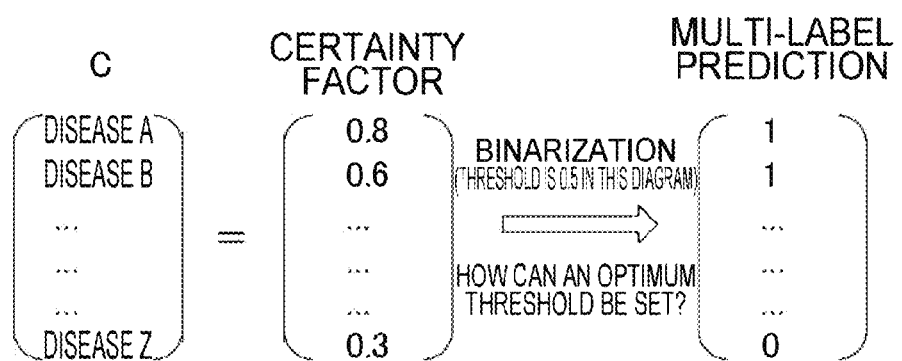
FIG. 9 is a schematic diagram explaining a binarization process of the inference apparatus according to one embodiment.

As an example of the first embodiment, FIG. 9 shows an example of using a same threshold of 0.5 for all diseases. In this case, the inference apparatus 20 predicts disease A and disease B having certainty factors larger than the threshold as candidate diseases, but does not designate disease Z having a certainty factor smaller than the threshold as a candidate disease. In the second embodiment, description has been given of usefulness of a threshold for each disease or a threshold for a group including multiple diseases.

To optimize the thresholds used to binarize the resulting certainty factors, attention is paid here to differences between data inputted during learning and data inputted during inference. For example, if learning data collected in facilities with a high prevalence rate is used during learning and the inference apparatus 20 is used in medical examination facilities with a low prevalence rate during inference, the distribution of input data will differ between when learning is being done and when inferences are being made. Also, if learning data collected in facilities where even a slight abnormality is determined to be a disease is used during learning and the inference apparatus 20 is used during inference in facilities where an obvious abnormality is determined to be a disease, even if the certainty factor is the same, there is a difference in determination of a candidate disease. Furthermore, because the fundus image used as learning data and the fundus image used for inference differ in photographic apparatus and photographic environment, even if the same patient is photographed around the same time, different fundus images are obtained under the influence of the photographic apparatus and the photographic environment.

Thus, the thresholds are optimized so as to minimize the above-mentioned differences between the environment in which learning data has been collected and the environment in which inferences are actually made as well as imbalance of the learning data.

If data during inference can be acquired, a threshold may be set for each disease so as to maximize a certain evaluation criterion in relation to a certainty factor obtained by inputting the image to be used for inference. For example, a threshold that maximizes a degree of separation between a case in which binarization is successful and a case in which binarization is unsuccessful may be set as an optimum threshold. Note that the evaluation criterion and algorithm for use to set the optimum threshold may be selected as desired. This will make it possible to minimize differences between an environment in which learning data has been collected and an environment in which inferences are actually made.

If data during inference cannot be acquired, by evaluating the accuracy of the inference apparatus 20 using k-fold cross-validation of learning data, the threshold may be set for each disease so as to maximize prediction accuracy. Note that in dividing learning data, it is desirable to use a technique that will reduce imbalance in data distribution between learning data and evaluation data. This will make it possible to accurately evaluate the prediction accuracy and set such a threshold that will maximize the prediction accuracy even when data during inference cannot be acquired.

REFERENCE SIGNS LIST

10 . . . learning apparatus, 110 . . . input unit, 120 . . . control unit, 121 . . . computational processing unit, 122 . . . memory, 123 . . . learning data acquisition unit, 124 . . . learning unit, 125 . . . image feature extraction unit, 126 . . . correlation feature extraction unit, 127 . . . model output unit, 128 . . . basis output unit, 130 . . . storage unit, 131 . . . learning data storage unit, 140 . . . communications unit, 20 . . . inference apparatus, 210 . . . input unit, 220 . . . control unit, 221 . . . computational processing unit, 222 . . . memory, 223 . . . model acquisition unit, 224 . . . basis acquisition unit, 225 . . . image acquisition unit, 226 . . . inference unit, 227 . . . image feature extraction unit, 228 . . . output unit, 230 . . . storage unit, 231 . . . image storage unit, 232 . . . learned model, 233 . . . classification basis, 240 . . . communications unit, 30 . . . storage apparatus, M1 . . . first machine learning model, M2 . . . second machine learning model, N . . . communications network

The invention claimed is:

1. An information processing apparatus comprising:
a processor configured to:
acquire a medical image;
extract one or more image feature values from the medical image;
infer one or more diseases predicted from the medical image based on the one or more image feature values and a classification basis, the classification basis being a set of C basis vectors with each basis vector representing correlations between a disease of a set of C diseases and other diseases by using a vector of a certain dimension, wherein C is an integer of 2 or more; and
output results identifying the one or more inferred diseases.

2. The information processing apparatus according to claim 1,
wherein the
processor is further configured to apply an activation function to a Hadamard product of the one or more image feature values and the classification basis to obtain respective certainty factors of the set of C diseases.

3. The information processing apparatus according to claim 1,
wherein the classification basis is obtained by causing a second machine learning model to do learning, where the second machine learning model accepts data embedded with label information about a plurality of medical images labeled with one or more diseases as input data, and outputs a feature that has learned correlations among diseases.

4. The information processing apparatus according to claim 3,
wherein the data accepted as the input data is graph data embedded with the label information about the plurality of medical images labeled with one or more diseases, the label information being in multi-hot vector form, and the second machine learning model is a graph convolutional neural network, with global max pooling (GMP) being applied in a final convolutional layer.

5. The information processing apparatus according to claim 4,
wherein the graph data includes a node corresponding to a disease or a lesion, and
wherein one or more lesions are inferred in addition to the one or more diseases from the medical images.

6. The information processing apparatus according to claim 2, wherein the processor is further configured to, when a certainty factor of each of the diseases obtained through inference is larger than a certain threshold, acquire such diseases as one or more candidate diseases.

7. The information processing apparatus according to claim 6, wherein the threshold is set for each disease, for a group including a plurality of diseases, or for a combination of each disease and the group.

8. The information processing apparatus according to claim 7, wherein the threshold is set so as to maximize a certain evaluation criterion for the certainty factor of each of the diseases obtained through inference.

9. The information processing apparatus according to claim 7,
wherein the one or more image feature values are acquired by inputting the medical image to a first learned model,
the first learned model is a learned model that has learned to estimate one or more image feature values from a medical image, and
wherein the threshold is set so as to maximize prediction accuracy of inferencing, the prediction accuracy being evaluated by k-fold cross-validation of learning data used in generating the first learned model.

10. A method comprising:
acquiring a medical image;
extracting one or more image feature values from the medical image;
inferring one or more diseases predicted from the medical image, based on the one or more image feature values and a classification basis, the classification basis being a set of C basis vectors with each basis vector representing correlations between a disease of a set of C diseases and other diseases by using a vector of a certain dimension, wherein C is an integer of 2 or more; and
outputting inferred results.

11. A non-transitory computer-readable recording medium recording a program that causes one or more computers to perform the processes of:
acquiring a medical image;
extracting one or more image feature values from the medical image;
inferring one or more diseases predicted from the medical image, based on the one or more image feature values and a classification basis, the classification basis being a set of C basis vectors with each basis vector representing correlations between a disease of a set of C diseases and other diseases by using a vector of a certain dimension, wherein C is an integer of 2 or more; and
outputting inferred results.

12. An information processing apparatus comprising:
a processor configured to:
generate a first machine learning model that outputs one or more image feature values from an image, the image feature value representing a feature of the image;
generate a second machine learning model that outputs a classification basis that has learned correlations among diseases from input data generated based on label information about a plurality of medical images labeled with one or more diseases;
cause the first machine learning model and the second machine learning model to do learning using the plurality of medical images labeled with one or more diseases, find certainty factors of the respective diseases based on the one or more image feature values acquired from the first machine learning model and the classification basis acquired from the second machine learning model, and cause the first machine learning model and the second machine learning model to do learning so as to minimize differences between the certainty factors and the diseases labeled to the medical images, the classification basis being a set of C basis vectors with each basis vector representing correlations between a disease of a set of C diseases and other diseases by using a vector of a certain dimension, wherein C is an integer of 2 or more;
output a learned model obtained through learning done by the first machine learning model; and
output the classification basis obtained through learning done by the second machine learning model.

13. A method comprising:
acquiring a plurality of medical images labeled with one or more diseases and a plurality of medical images free of diseases;
causing a first machine learning model and a second machine learning model to do learning using the medical images, the first machine learning model being a machine learning model that outputs one or more image feature values from an image, the image feature value representing a feature of the image, the second machine learning model being a machine learning model that outputs a classification basis that has learned correlations among diseases from input data generated based on label information about the plurality of medical images labeled with one or more diseases, finding certainty factors of the respective diseases based on the one or more image feature values acquired from the first machine learning model and the classification basis acquired from the second machine learning model, and causing the first machine learning model and the second machine learning model to do learning so as to minimize differences between the certainty factors and the diseases labeled to the medical images, the classification basis being a set of C basis vectors with each basis vector representing correlations between a disease of a set of C diseases and other diseases by using a vector of a certain dimension, wherein C is an integer of 2 or more;
outputting a learned model obtained through learning done by the first machine learning model; and
outputting the classification basis obtained through learning done by the second machine learning model.

* * * * *